(12) United States Patent
Wingardner, III et al.

(10) Patent No.: US 8,262,620 B2
(45) Date of Patent: *Sep. 11, 2012

(54) MULTI-LUMEN ACCESS PORT

(75) Inventors: Thomas Wingardner, III, North Haven, CT (US); Gene A. Stellon, Burlington, CT (US); Robert J. DeSantis, Redding, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/089,340

(22) Filed: Apr. 19, 2011

(65) Prior Publication Data
US 2011/0190590 A1    Aug. 4, 2011

Related U.S. Application Data

(63) Continuation of application No. 12/468,363, filed on May 19, 2009, now Pat. No. 7,951,117.

(60) Provisional application No. 61/075,542, filed on Jun. 25, 2008.

(51) Int. Cl.
*A61M 5/178* (2006.01)

(52) U.S. Cl. .................... 604/164.09; 604/174; 606/108

(58) Field of Classification Search ............. 604/164.01, 604/164.03, 164.09, 174, 175, 264; 606/108, 606/215

See application file for complete search history.

(56) References Cited

U.S. PATENT DOCUMENTS

| | | | |
|---|---|---|---|
| 4,016,884 A | 4/1977 | Kwan-Gett | |
| 4,112,932 A | 9/1978 | Chiulli | |
| 4,402,683 A | 9/1983 | Kopman | |
| 5,183,471 A | 2/1993 | Wilk | |
| 5,269,772 A | 12/1993 | Wilk | |
| 5,366,478 A | 11/1994 | Brinkerhoff et al. | |
| 5,375,588 A | 12/1994 | Yoon | |
| 5,480,410 A | 1/1996 | Cuschieri et al. | |
| 5,507,758 A | 4/1996 | Thomason et al. | |
| 5,540,648 A | 7/1996 | Yoon | |
| 5,653,705 A | 8/1997 | de la Torre et al. | |
| 5,672,168 A | 9/1997 | de la Torre et al. | |
| 5,683,378 A | 11/1997 | Christy | |
| 5,795,290 A | 8/1998 | Bridges | |
| 5,836,871 A | 11/1998 | Wallace et al. | |
| 5,848,992 A | 12/1998 | Hart et al. | |
| 5,906,577 A | 5/1999 | Beane et al. | |
| 5,957,913 A | 9/1999 | de la Torre et al. | |
| 6,024,736 A | 2/2000 | de la Torre et al. | |
| 6,086,603 A | 7/2000 | Termin et al. | |
| 6,099,506 A | 8/2000 | Macoviak et al. | |
| 6,142,936 A | 11/2000 | Beane et al. | |
| 6,217,555 B1 | 4/2001 | Hart et al. | |

(Continued)

FOREIGN PATENT DOCUMENTS

EP    1312318    4/1998

(Continued)

*Primary Examiner* — Laura Bouchelle

(57) ABSTRACT

An access device includes a body, a first tube, a second tube, and a mechanism. The first and second tubes extend through the body. The mechanism operably couples the first and second tubes such that at least one tube is pivotable about an axis with respect to the other tube. The body may form a substantially fluid-tight seal at the incision. In another embodiment, the access device further includes a third tube extending through the body and the mechanism operably couples the tubes together such that at least two tubes are pivotable about the axis with respect to the remaining tube.

19 Claims, 1 Drawing Sheet

U.S. PATENT DOCUMENTS

| | | |
|---|---|---|
| 6,315,770 B1 | 11/2001 | de la Torre et al. |
| 6,319,246 B1 | 11/2001 | de la Torre et al. |
| 6,371,968 B1 | 4/2002 | Kogasaka et al. |
| 6,440,061 B1 | 8/2002 | Wenner et al. |
| 6,440,063 B1 | 8/2002 | Beane et al. |
| 6,454,783 B1 * | 9/2002 | Piskun ............ 606/185 |
| 6,488,620 B1 | 12/2002 | Segermark et al. |
| 6,488,692 B1 | 12/2002 | Spence et al. |
| 6,551,270 B1 * | 4/2003 | Bimbo et al. ......... 604/93.01 |
| 6,669,674 B1 | 12/2003 | Macoviak et al. |
| 6,706,050 B1 | 3/2004 | Giannadakis |
| 6,725,080 B2 | 4/2004 | Melkent et al. |
| 6,840,951 B2 | 1/2005 | de la Torre et al. |
| 6,863,674 B2 | 3/2005 | Kasahara et al. |
| 6,913,609 B2 | 7/2005 | Yencho et al. |
| 6,997,909 B2 | 2/2006 | Goldberg |
| 7,008,377 B2 | 3/2006 | Beane et al. |
| 7,014,628 B2 | 3/2006 | Bousquet |
| 7,101,353 B2 | 9/2006 | Lui et al. |
| 7,223,257 B2 | 5/2007 | Shubayev et al. |
| 7,235,084 B2 | 6/2007 | Skakoon et al. |
| 7,344,547 B2 | 3/2008 | Piskun |
| 7,951,117 B2 * | 5/2011 | Wingardner et al. .... 604/164.09 |
| 2003/0028179 A1 | 2/2003 | Piskun |
| 2004/0167543 A1 | 8/2004 | Mazzocchi et al. |
| 2006/0020241 A1 | 1/2006 | Piskun et al. |
| 2006/0161049 A1 | 7/2006 | Beane et al. |
| 2006/0241651 A1 | 10/2006 | Wilk |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0270911 A1 | 11/2006 | Voegele et al. |
| 2007/0118175 A1 | 5/2007 | Butler et al. |
| 2007/0208312 A1 | 9/2007 | Norton et al. |
| 2008/0027476 A1 | 1/2008 | Piskun |
| 2008/0255519 A1 | 10/2008 | Piskun et al. |
| 2009/0012477 A1 | 1/2009 | Norton et al. |

FOREIGN PATENT DOCUMENTS

| | | |
|---|---|---|
| EP | 2044889 | 10/2008 |
| WO | 93/14801 | 8/1993 |
| WO | 94/04067 | 3/1994 |
| WO | 97/42889 | 11/1997 |
| WO | 99/16368 | 4/1999 |
| WO | 2008015566 | 2/2008 |
| WO | 2008121294 | 10/2008 |

* cited by examiner

_US 8,262,620 B2_

MULTI-LUMEN ACCESS PORT

CROSS-REFERENCE TO RELATED APPLICATIONS

This application is a continuation of U.S. patent application Ser. No. 12/468,363, filed on May 19, 2009 now U.S. Pat. No. 7,951,117, which claims the benefit of, and priority to, U.S. Provisional Patent Application Ser. No. 61/075,542, filed on Jun. 25, 2008, the entire contents of each application being incorporated by reference herein in its entirety.

BACKGROUND

1. Technical Field

The present disclosure relates to access devices and, more particularly, to a multi-lumen access port.

2. Background of Related Art

During laparoscopic surgery, a surgeon performs surgical procedures through small incisions. Typically, these incisions measure about half an inch. The surgeon also places small ports through the incisions to gain access into the abdominal cavity of the patient. These ports have a number of uses. For example, a surgeon may use a port for insufflating the abdominal cavity to create space, another port for introducing a laparoscope for viewing, and a number of other ports for introducing surgical instruments for operating on tissue. Generally, laparoscopic surgery costs less than open surgery. In addition, patients typically recover faster from a laparoscopic surgery than from an open surgery.

In open surgery, surgeons use their hands, together with surgical instruments, to manipulate tissue. Surgeons performing open surgery may decide to perform particular steps of the procedure with their hands and other steps with surgical instruments. For instance, open surgery allows surgeons to obtain tactile feedback through their fingertips. Surgeons may also use their hands to remove relatively large portions of tissue from a body cavity. Moreover, open surgery facilitates the use of relatively large surgical instruments within the human body.

SUMMARY

The present disclosure relates to an access device. The access device includes a body, a first tube, a second tube, and a mechanism. The first and the second tubes extend through the body of the access device. The mechanism operably couples the first and second tubes such that at least one tube is pivotable about an axis with respect to the other. The proximal ends of the first and second tubes are located within the body. At least one of the tubes extends distally from a surface of the body. The body may be adapted for placement in an opening in body tissue. During use, body may form a substantially fluid-tight seal at the opening or incision. The access device may further include a third tube extending through the body. In this embodiment, the mechanism operably couples the tubes together such that at least two tubes are pivotable about the axis with respect to the remaining tube.

BRIEF DESCRIPTION OF THE DRAWINGS

Embodiments of the presently disclosed multi-lumen access port are described herein with reference to the accompanying drawings, wherein.

DETAILED DESCRIPTION OF EMBODIMENTS

Figure 1:
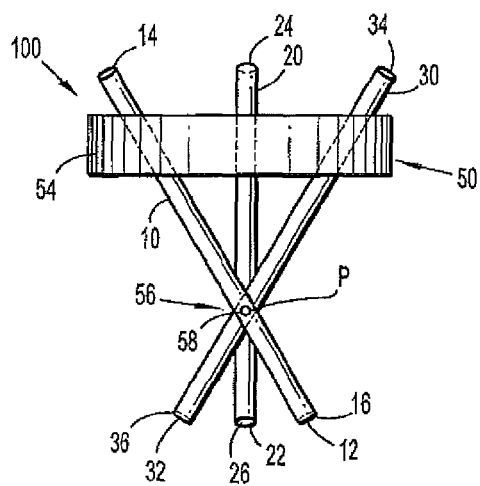
FIG. 1 is side view of an embodiment of the presently disclosed multi-lumen access port.

Embodiments of the presently disclosed multi-lumen access port will now be described in detail with reference to the drawing figures wherein like reference numerals identify similar or identical elements. In the drawings and in the description which follows, the term "proximal", as is traditional, will refer to the end of the multi-lumen access port which is closest to the operator while the term "distal" will refer to the end of the device which is farthest from the operator.

Referring initially to FIG. 1, the presently disclosed multi-lumen access port is shown generally as access port 100. Access port 100 includes a plurality of access tubes 10, 20, 30. One or more of the access tubes 10, 20, 30 may contain a fluid-tight seal. Each access tube 10, 20, 30 has an open proximal end 14, 24, 34 and an open distal end 16, 26, 36. A passageway 12, 22, 32 is defined between open proximal ends 14, 24, 34 and open distal ends 16, 26, 36. Each access tube 10, 20, 30 is generally an elongate tubular structure that is adapted for receiving at least a portion of an endoscopic surgical instrument (not shown) therethrough. In one embodiment, the configuration of at least one passageway 12, 22, 33 allows passage of a surgical instrument having an outside diameter ranging between about 5 mm and about 12 mm through access tubes 10, 20, 30. Access tubes 10, 20, 30 may be configured, however, to receive surgical instruments having other suitable sizes. The present disclosure envisions access tubes 10, 20, 30 having a variety of sizes and shapes. Access tubes 10, 20, 30 may have circular cross-sections, oval cross-sections, or any other suitable shape so long as they are capable of receiving a surgical instrument. In addition to their ability to receive a surgical instrument, access tubes 10, 20, 30 are able to move axially with respect to one another.

Access port 100 includes a mechanism 56 adapted to facilitate relative movement of access tubes 10, 20, 30. Mechanism 56 operably connects access tubes 10, 20, 30 at a pivot point P. Consequently, a portion of each access tube 10, 20, 30 overlaps at pivot point P. The location of pivot pin P allows users to employ mechanism 56 to pivot access tubes 10, 20, 30 with respect to one another. In the depicted embodiment, mechanism 56 includes a pivot pin 58 or any other suitable fastening member adapted to interconnect access tubes 10, 20, 30. Pivot pin 58 facilitates pivotal movement of access tubes 10, 20, 30 about an axis. Alternatively, pivot pin 58 operably couples only two access tubes 10, 20. In any case, the location of pivot pin 58 coincides with the location of pivot point P. Accordingly, access tubes 10, 20, 30 rotate about pivot point P upon manipulation by a user during operation.

Figure 2:
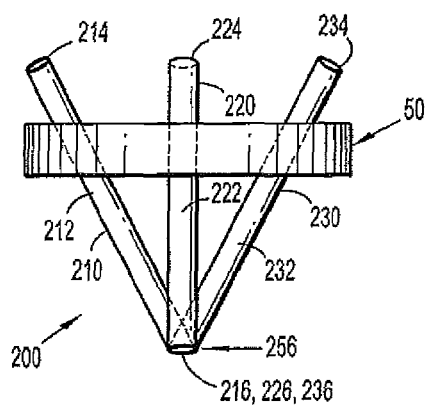
FIG. 2 is a side view of an alternate embodiment of the presently disclosed multi-lumen access port.

FIG. 2 illustrates an alternate embodiment of the present disclosure. This embodiment is generally designated as access port 200. Access port 200 is substantially similar to access port 100. The presently disclosed access port 200 includes a plurality of access tubes 210, 220, 230. At least one access tube 210, 220, 230 may include a fluid-tight seal. Each access tube 210, 220, 230 has an open proximal ends 214, 224, 234 and an open distal end 216, 226, 236. Open proximal ends 214, 224, 234 and open distal ends 216, 226, 236 each defines a passageway 212, 222, 232 therebetween. Each passageway 212, 222, 232 has a cross-section adapted to receive an endoscopic surgical instrument. In one embodiment, the cross-section of at least one passageway 212, 222, 232 is capable of receiving therethrough a surgical instrument having an outside diameter ranging between about 5 mm and about 12 mm. During use, a surgeon may introduce a surgical instrument through open proximal end 214, 224, 234 until it reaches a location beyond open distal ends 216, 226, 236.

The open distal ends 216, 226, 236 of access port 200 form a juncture 256, as illustrated in FIG. 2. Juncture 256 operatively connects open distal ends 216, 226, 236 with one another. During operation, juncture 256 facilitates relative movement of access tubes 210, 220, 230 upon manipulation by a user. Therefore, juncture 264 is sufficiently strong to maintain open distal ends 216, 226, 236 joined, but sufficiently flexible to allow relative movement of access tubes 210, 220, 230.

As seen in FIGS. 1 and 2, the embodiments of the present disclosure include a support body 50. Support body 50 supports access tubes 10, 20, 30. In use, support access 50 serves as a standalone component for providing access to a working space in the patient's body. Alternatively, a user may use support body 50 in conjunction with other access devices (i.e. access ports). In any case, support body 50 has a flexible outer wall 54. The resiliency of flexible outer wall 54 permits temporarily deformation of support body 50 during its installation. After installation, support body 50 along with its flexible outer wall 54 reverts to its original configuration and provides a fluid-tight seal in conjunction with the patient's skin (i.e. standalone mode) or the access device. In either mode, support body 50 conforms to the skin at an opening in the patient's body or the interior wall of the access device, thereby providing a fluid-tight seal for inhibiting leakage of insufflation fluids from the working space or the introduction of external contaminants into the working space.

The structural relationships between support body 50 and access tubes 10, 20, 30 is substantially similar to the structural relationship between support body 50 and access tubes 210, 220, 230. Therefore, the mechanical cooperation and operation of support body 50 and access tubes 210, 220, 230 will not be described herein in detail.

Figure 3:
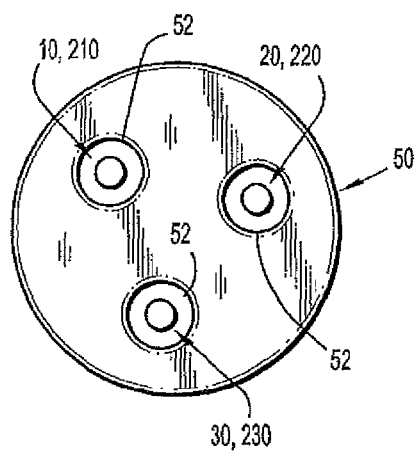
FIG. 3 is a top view of the embodiments of FIGS. 1 and 2.
Figure 4:
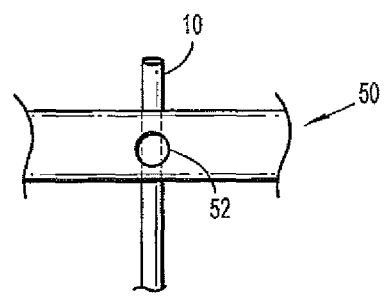
FIG. 4 is a cross-sectional side view of an access tube and a portion of a support body according to an embodiment of the present disclosure.

Referring to FIGS. 3 and 4, an embodiment of support body 50 has a circular cross-section. The present disclosure nevertheless envisions support bodies with other configurations. In the depicted embodiment, support body 50 includes a plurality of bores 52. Bores 52 are laterally and longitudinally spaced apart from one another. Each bore 52 is adapted to receive an access tube 10, 20, 30 and extends through support body 50. The cross-section of each bore 55 is larger than the cross-section of access tubes 10, 20, 30, as seen in FIGS. 3 and 4. This configuration provides access tubes 10, 20, 30 certain freedom of movement within bores 52.

Figure 5:
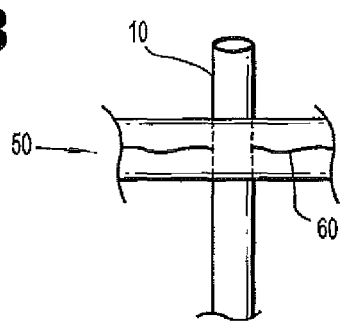
FIG. 5 is a cross-sectional side view of an access tube and a portion of a support body according to another embodiment of the present disclosure.

In an alternative embodiment, support body 50 includes at least one slit 60 extending along at least a portion of the length of support body 50, as illustrated in FIG. 5. Slit 60 enhances the flexibility of support body 50. The presence of slit 60 allows user to move access tubes 10, 20, 30 beyond the boundaries of bores 52.

In use, a surgeon may employ access port 100 or 200 to create and maintain access into a working space inside a patient's body during a surgical procedure. In particular, physicians may employ either access port 100, 200 during a laparoscopy or a HALS procedure. Initially, the surgeon may first incise a body wall with scalpel or any other suitable instrument. Alternatively, the surgeon may penetrate the body wall with a sharp tip. Once the body wall has an opening, the surgeon may place support body 50 in the desired site.

The physician may employ support body 50 by itself or in conjunction with other access device. Before placing access port 100 inside a patient's body, the surgeon may deform support body 50. Thereafter, the surgeon places access port 100 inside the patient's body.

Immediately after its installation, support body 50 reverts to its original configuration and creates a fluid-tight seal in conjunction with the patient's skin (in the standalone mode) or an access device. After the establishing the fluid-tight seal, the surgeon inserts one or more surgical instruments through access tubes 10, 20, 30. In particular, the surgeon may initially insert an insufflation device through any access tube 10, 20, 30. Before activating the insufflation device, the user may move access tubes 10, 20, 20 to direct the delivery of insufflation gas. Once in position, the insufflation device delivers gas to a body cavity upon activation by the surgeon. This gas expands the body cavity and prepares the surgical site. Subsequently, the physician may insert a laparoscope or any other suitable viewing apparatus through another access tube 10, 20, 30. The laparoscope facilitates visual observation of the surgical site. Again, the operator may move access tubes 10, 20, 30 to observe several areas of the body cavity. After visually inspection the body cavity, the physician may insert a surgical instrument through any of the open proximal ends 14, 24, 34. The surgeon should advance the surgical instrument through the corresponding passageway 12, 22, 32 until it reaches a location beyond corresponding open distal end 16, 26, 36. The surgeon may then move access tubes 10, 20, 30 to reach the desired surgical site.

Access tubes 10, 20, 30 may move upon manual manipulation by the operator. The operator, however, may use any suitable means to move access tubes 10, 20, 30. During operation, access tubes 10, 20, 30 of access port 100 move relative to one another about pivot point "P." The boundaries of bores 52 may slightly restrict the movement of access tubes 10, 20, 30, as shown in FIG. 4. Nonetheless, access tubes disposed in a support body 50 having a slit 60 may easily move beyond the boundaries of bores 52.

The method of using access port 100 is substantially similar to the method of using access port 200. During the operation of access port 200, however, a surgeon may move access tubes 210, 220, 230 with respect to one another, but their distal open ends 216, 226, 236 are fixed in relation to each other.

It will be understood that various modifications may be made to the embodiments of the presently disclosed surgical stapling instruments. Therefore, the above description should not be construed as limiting, but merely as exemplifications of embodiments. Those skilled in the art will envision other modifications within the scope and spirit of the present disclosure.

What is claimed is:

1. An access device comprising:
   a body portion;
   a first tube extending through the body portion, the first tube having a proximal end, a distal end, and a longitudinal passageway extending therethrough; and
   a second tube extending through the body portion, the second tube having a proximal end, a distal end, and a longitudinal passageway extending therethrough, the first and second tubes being secured together adjacent the distal ends thereof to define a juncture, the juncture permitting relative movement between the first and second tubes to allow for selective orientation of the first and second tubes to facilitate performance of a surgical procedure with surgical instrumentation introduced through at least one of the first and second tubes, wherein the body includes a proximal surface and a distal surface, the juncture being positioned distally of the distal surface.

2. The access device of claim 1, wherein body portion is of unitary construction.

3. The access device of claim 1, wherein the body portion includes a first bore extending therethrough configured and dimensioned to receive the first tube, and a second bore extending therethrough configured and dimensioned to receive the second tube.

4. The access device of claim 1, wherein the proximal ends of the first and second tubes are located within the body, the distal end of at least one of the first and second tubes extending distally from the body.

5. The access device of claim 1, wherein the body is configured and dimensioned for placement in an opening in body tissue.

6. The access device of claim 5, wherein the body is dimensioned and adapted to form a substantially fluid-tight seal at the opening.

7. The access device of claim 6, wherein at least one of the first and second tubes includes a seal member configured and dimensioned to form a substantially fluid-tight seal with inserted surgical instrumentation.

8. The access device of claim 1, further comprising a third tube extending through the body and having proximal and distal ends, the juncture securing together the first, second, and third tubes adjacent the distal ends thereof such that at least two of the first, second, and third tubes are movable with respect to the other of the first, second, and third tubes.

9. The access device of claim 8, wherein the body portion includes a first bore extending therethrough configured and dimensioned to receive the first tube, a second bore extending therethrough configured and dimensioned to receive the second tube, and a third bore extending therethrough configured and dimensioned to receive the third tube.

10. The access device of claim 1, wherein the juncture is formed such that relative longitudinal movement between the first and second tubes is substantially inhibited.

11. The access device of claim 1, wherein the body portion is formed from a flexible material.

12. An access device comprising:
a body portion having proximal and distal surfaces;
a first tube having proximal and distal ends, and extending through the body portion;
a second tube having proximal and distal ends, and extending through the body portion; and
a juncture operably coupling the first and second tubes together such that relative longitudinal movement between the first and second tubes is substantially inhibited, the juncture being positioned distally of the distal surface of the body portion.

13. The access device of claim 12, wherein the juncture is configured and dimensioned to permit relative transverse movement between the first and second tubes.

14. The access device of claim 12, wherein body portion is of unitary construction.

15. The access device of claim 12, wherein the proximal ends of the first and second tubes are located within the body portion, the distal end of at least one of the first and second tubes extending distally from the body portion.

16. The access device of claim 12, wherein the body portion includes a first bore extending therethrough configured and dimensioned to receive the first tube, and a second bore extending therethrough configured and dimensioned to receive the second tube.

17. The access device of claim 12, further comprising a third tube extending through the body and having proximal and distal ends, the juncture securing together the first, second, and third tubes adjacent the distal ends thereof such that at least two of the first, second, and third tubes are movable transversely with respect to the other of the first, second, and third tubes.

18. The access device of claim 17, wherein the body portion includes a first bore extending therethrough configured and dimensioned to receive the first tube, a second bore extending therethrough configured and dimensioned to receive the second tube, and a third bore extending therethrough configured and dimensioned to receive the third tube.

19. A method of assembling a surgical access system comprising:
inserting a first tube into a body with proximal and distal surfaces that is configured and dimensioned for positioning within an opening in tissue; inserting a second tube into the body; and
securing the first and second tubes together at a juncture positioned distally of the distal surface of the body such that relative longitudinal movement between the first and second tubes is substantially inhibited.

* * * * *